(12) United States Patent
Muller et al.

(10) Patent No.: US 7,276,207 B2
(45) Date of Patent: Oct. 2, 2007

(54) MICROSYSTEM FOR THE DIELECTRIC AND OPTICAL MANIPULATION OF PARTICLES

(75) Inventors: Torsten Muller, Berlin (DE); Thomas Schnelle, Berlin (DE); Gunter Fuhr, Berlin (DE)

(73) Assignee: Evotec Technologies GmbH, Dusseldorf (DE)

( * ) Notice: Subject to any disclaimer, the term of this patent is extended or adjusted under 35 U.S.C. 154(b) by 811 days.

(21) Appl. No.: 10/432,793

(22) PCT Filed: Nov. 28, 2001

(86) PCT No.: PCT/EP01/13901

§ 371 (c)(1),
(2), (4) Date: Sep. 5, 2003

(87) PCT Pub. No.: WO02/43870

PCT Pub. Date: Jun. 6, 2002

(65) Prior Publication Data

US 2004/0063196 A1    Apr. 1, 2004

(30) Foreign Application Priority Data

Nov. 29, 2000  (DE) ............................... 100 59 152

(51) Int. Cl.
*B01L 3/00* (2006.01)
*G01N 27/447* (2006.01)
*G01N 27/453* (2006.01)

(52) U.S. Cl. .......................... 422/99; 204/600; 204/601

(58) Field of Classification Search ................ 204/600, 204/450, 547, 643; 422/68.1, 99, 100
See application file for complete search history.

(56) References Cited

U.S. PATENT DOCUMENTS 5,100,627 A * 3/1992 Buican et al. ............... 422/108

(Continued)

FOREIGN PATENT DOCUMENTS

DE    195 00 660 A1    6/1996

(Continued)

OTHER PUBLICATIONS

Sanders et al., "Chip-based microsystems for genomic and proteomic analysis," *Trends in Analytica Chemistry*, vol. 19, No. 6 (2000).

(Continued)

*Primary Examiner*—Alex Noguerola
(74) *Attorney, Agent, or Firm*—Caesar, Rivise, Bernstein, Cohen & Pokotilow, Ltd.

(57) ABSTRACT

Described is a fluidic microsystem with at least one compartment for the receiving and/or the through-flow of a liquid and having an electrode arrangement with a multiplicity of electrodes, between which a coaction zone is established, whereby the compartment possesses at least one wall, through which electromagnetic radiation can be linked into the said coaction zone in accord with a predetermined incident direction, and on at least one electrode a cooling apparatus is provided, and on which at least one respective electrode at least one reflector layer is provided, and wherein the respective electrode is at least partially shielded in reference to the incident beam direction, and having at least one heat conducting layer by means of which the respective electrode stands in thermal communication with a wall of the compartment, and/or includes an active cooling element, which is placed in thermal contact with the respective electrode.

14 Claims, 3 Drawing Sheets

U.S. PATENT DOCUMENTS

| | | | |
|---|---|---|---|
| 6,056,861 A | | 5/2000 | Fuhr et al. |
| 6,074,605 A | * | 6/2000 | Meserol et al. ............... 422/33 |
| 6,492,175 B1 | | 12/2002 | Müller et al. |
| 6,663,757 B1 | * | 12/2003 | Fuhr et al. .................. 204/450 |
| 6,797,524 B1 | * | 9/2004 | Seul ........................... 436/526 |
| 7,081,192 B1 | * | 7/2006 | Wang et al. ................ 204/547 |

FOREIGN PATENT DOCUMENTS

| | | |
|---|---|---|
| DE | 196 05 830 C1 | 2/1997 |
| DE | 195 44 127 C1 | 3/1997 |
| DE | 196 02 786 A1 | 7/1997 |
| DE | 196 53 659 C1 | 5/1998 |
| DE | 198 15 882 A1 | 10/1999 |
| DE | 198 59 459 A1 | 6/2000 |
| WO | WO 00 28 313 A1 | 5/2000 |

OTHER PUBLICATIONS

Schnelle et al., "Combined dielectrophoretic filed cages and laser tweezers for electrorotation," *Applied Physics B*, 70, pp. 267-274 (2000).

Schütze et al., "Laser micromanipulation systems as universal tool in cellular and molecular biology and in medicine," *Cellular and Molecular Biology*, vol. 44(5), pp. 735-746 (1998).

Ashkin et al., "Optical trapping and manipulation of single cells using infrared laser beams," *Nature*, vol. 330, pp. 769-771 (Dec. 24-31, 1987).

De Gasperis et al., "Automated electrorotation: dielectric characterization of living cells by real-time motion estimation," *Meas Sci. Technol.*, 9, pp. 518-529 (1998).

Ehrfeld et al., "Microreactors for Chemical Synthesis and Biotechnology—Current Developments and Future Applications," *Topics in Current Chemistry*, vol. 194, p. 233, 1998.

Fromherz et al., "A Neuron-Silicon Junction: A Retzius Cell of the Leech on an Insulated-Gale Field-Effect Transistor," *Science*, vol. 252, pp. 1290-1293 (May 31, 1991).

Fuhr, et al., "Living cells in opto-electrical cages," *Trends in Analytical Chemistry*, vol. 19, No. 6, pp. 402-408 (2000).

Fuhr, et al. "Force measurement of optical tweezers in electro-optical cages," *Applied Physics A*, vol. 67, pp. 385-390 (1998).

Fuhr et al., "Biological Application of Microstructures," *Topics in Current Chemistry*, vol. 194, pp. 83-116 (1998).

Giaever et al., "Micromotion of mammalian cells measured electrically," *Proc. Natl. Acad. Sci.*, vol. 88, pp. 7896-7900 (Sep. 1991).

* cited by examiner

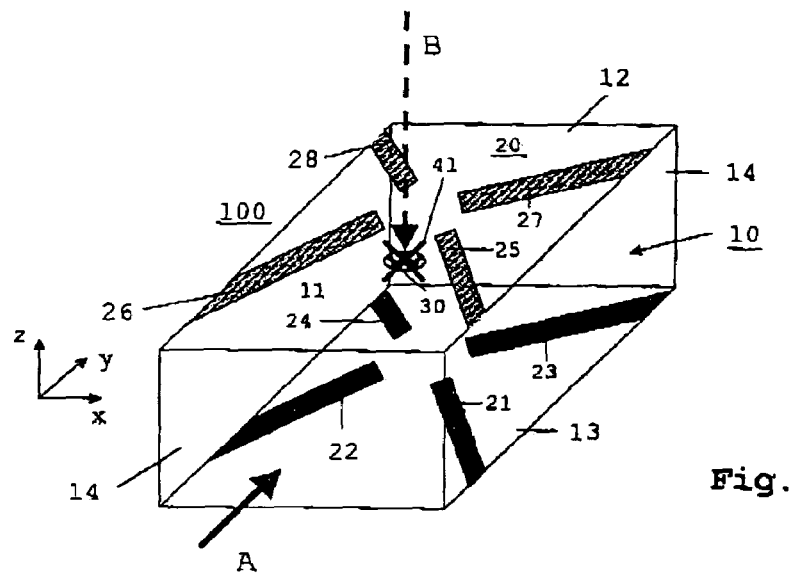
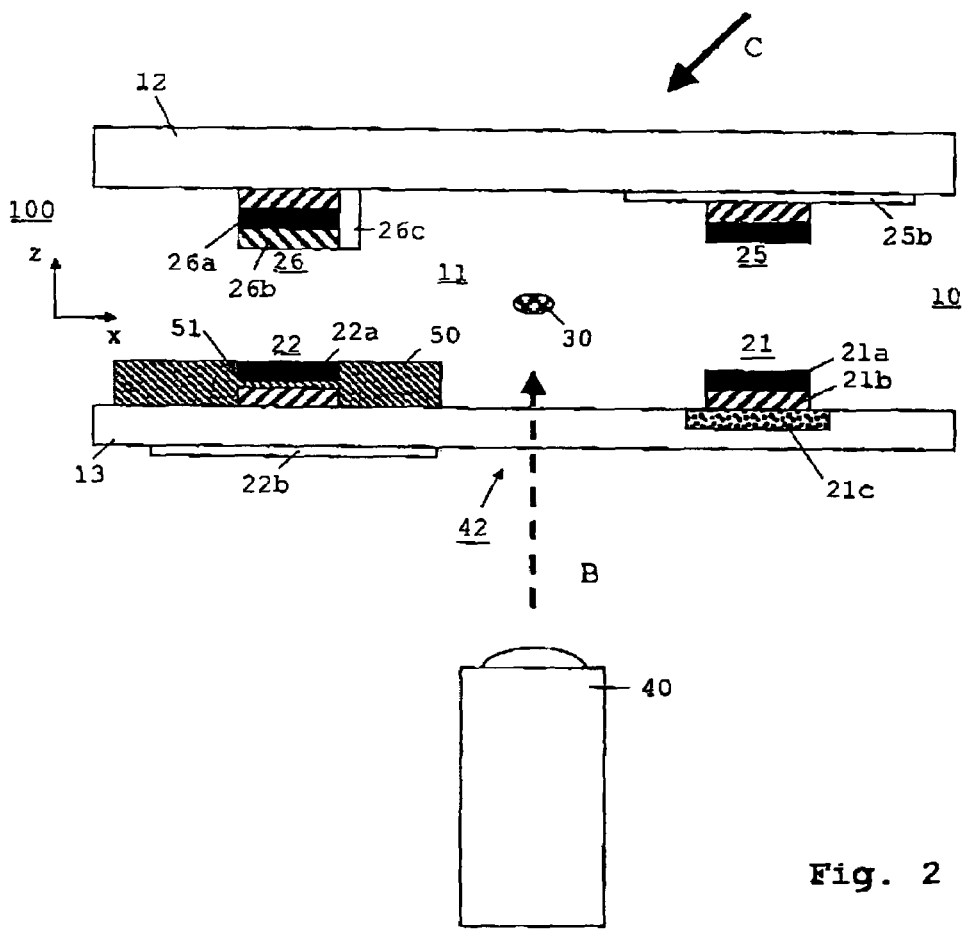
Fig. 1
Fig. 2

MICROSYSTEM FOR THE DIELECTRIC AND OPTICAL MANIPULATION OF PARTICLES

This application is a 371 of PCT/EP01/13901, filed on Nov. 28, 2001, and claims priority from German patent application DE 10059152.3, filed on Nov. 29, 2000.

BACKGROUND OF THE INVENTION

The invention concerns a microsystem for the dielectric and optical manipulation of suspended particles, such as, for example, a fluid microsystem for the measurement and treatment of biological or synthetic particles, and further concerns the use of reflection shielding materials in microsystems, which material is designed to minimize the effect of electric and optical field forces on suspended particles.

Fluidic and liquid filled microsystems have multitudinous applications in biochemistry, medicine and biology, especially for the analysis and manipulation of dissolved substances or suspended particles. By means of the miniaturization and massive parallelism of the processes running in Microsystems (or microchips), particular advantages arise for the analysis and synthesis of biological macromolecules which are present in higher combinatorial multiplicity (refer to G. H. Sanders et al., in *Trends in Analytical Chemistry*, vol. 19/6, 2000, pg. 364 ff; W. Ehrfeld in *Top ics in Current Chemistry*, publisher A Manz et al., vol 194, Springer Verlag, 1988, pg. 233. ff). Applications in the fluidic microsystem especially encompass fundamental research, such as is found in DNA analysis or protein analysis, or even in active substance research including combinatorial chemistry. Further applications arise in the analysis and manipulation of individual biological cells or cell groups (see G. Führ et al., in *Top ics in Current Chemistry*, publisher A. Manz et al. vol. 194, Springer Verlag, 1998, pg. 83 ff).

Many applications of fluidic microsystems in cell biology, medicine, pharmaceuticals and biotechnology, are directed toward suspended particles, which are to be manipulated while subjected to the effects of electrical field forces (for instance, to evaluate, to measure, to divide, to move or to treat). The electrical field forces are produced with the aid of electrode arrangements of microelectrodes, which are specifically placed in accord with the application and the purpose of the task. The microelectrodes possess typical dimensions in the micromillimeter range. Other applications of microsystems are directed to the capture of the character of biological cells, which stand in direct contact with the microelectrodes (see, for example, B. I. Giaver et al., in *Procedures of the National Academy of Sciences*, vol. 88, 1991, pg. 7896, or refer to P. Fromherz et al., in *Science* vol. 252, 1991, pg. 1290.

An interest has developed, in the manipulation of microscopically small particles, of applying forces which are as independent as possible from electrical field influences. This effort has been described in *Applied Physics A*, by G. Fuhr, et al., vol. 67, 1998, page 385 and in *Applied Physics B*, by Th. Schnelle et al., *Applied Physics B*, vol 70, 2000, page 267.

In cell biology and molecular biology, with increasing frequency, particles are subjected to forces with the so-called laser-tweezers or with the UV-laser beam in microsurgery, wherein the said forces are generated by a focused illumination. Such forces are known as "optical forces". The laser-tweezer (see A. Ashkin et al., in *Nature*, vol. 330, 1987, page 769) is based on the following principle:

A sharply focused laser beam is directed onto an objective with a high numerical aperture (>1), in a coaction zone, which, for instance, is to be found in a microsystem or another reservoir. Microparticles and especially biological cells in a range of size of from some 10 nm to some 10 μm are captured in the focus, and can be moved with displacement of the laser beam. In order that the beam loading be held as low as possible, especially on biological materials, the optical laser tweezers are operated at a wavelength in the range of 700 nm to 1064 nm. Optical tweezers are employed, for instance, for adhesion investigations on particles (refer to G. Fuhr. et al., in *Trends in Analytical Chemistry*, vol. 19/6, 2000, pg. 402, for positioning for fusion or poration-procedures on biological cells, see K. Schütze et al., in *Cell. Mol. Biol.*, vol. 44/5, 1998, pg. 735) and in fluidic Microsystems with dielectrical particle manipulation, such as, for example dielectric field forces (G. Fuhr et al., Th. Schnelle et al., see above) or in rotation chambers (refer to DeGasperis, et al., in *Meas. Sci. Technol.*, vol. 9, 1998, pg. 518).

The incident radiating of light is carried out in the case of Microsystems not only to achieve manipulation, but also for purposes of analysis. This involves a linking incidence of a laser beam to activate a fluorescence marker or to execute spectroscopic measurements on given particles.

A general problem present in the penetration of light into microsystems with electrode arrays is to be found therein, in that the electrodes can be heated by the said radiation. If, for example, a focused infrared laser beam invades or impacts the neighborhood (here in the micromillimeter range) of the surface of electrodes, this leads to a heating of the electrodes, more or less depending on the material of the electrode material and its inherent absorption and reflection characteristics. The result is often a localized buildup of gas bubbles (see A. Elshabini et al., in *Thin Film Technology Handbook*, McGraw-Hill Companies, 1998, ISBN 0-07-019025-9). Particularly strong absorption occurs with such materials as titanium, tantalum, and platinum. Not only the electrodes, but the contingent medium, such as the suspension liquid or a cell prone to adsorption are heated. This can lead to massive disturbances of the function of the microsystem under investigation.

For instance, in fluidic micro systems, which, for example, are energized for dielectrical particle manipulation with high frequency electrical voltages for the generation of higher field gradients (for instance, 1 kV/m, 1 Hz to 10 MHz), heating of electrodes can cause electro-hydro-dynamic flows within the suspension fluid, which are detrimental to, or indeed make fully impossible, a desired particle manipulation by the coaction of electric and optical field forces. Additionally, the formation of gas bubbles leads to stressing and destruction of the electrode material. Shock waves can be induced, which in turn burden the cells with undesirable pressure and current effects.

Corresponding problems also appear in Microsystems, in which the particles make direct contact with the electrodes. This event can cause local heating, under the action of which, for instance, cells sensitive to being adsorbed die off.

Thus the purpose of the invention is to make available an improved micro system for particle manipulation, which functions under the action of electrical and optical field forces, wherein the disadvantages of the conventional microsystems are overcome and in which, especially undesirable heating by external radiation of the electrodes is avoided, or reduced. The invented microsystem should make possible a reliable coaction of optical and electrical field forces on suspended particles without the formation of disturbing liquid movements.

SUMMARY OF THE INVENTION

The basic concept of the invention is to provide at least one cooling apparatus, in a microsystem, which is designed for the combined effect of electrical and optical forces upon microscopically small particles, on one or more electrodes, especially at electrode ends, upon which falls, in some cases, linking electromagnetic radiation, especially light, for the exertion of electrical force. The cooling apparatus is formed by one or more of the following measures:

First, provision is made, for the use of at least one reflector layer for at least partial shielding of electrode surfaces against at least one light beam linkingly entering the microsystem. The at least one reflector layer possesses the advantage, that it avoids the heating of an electrode by radiation, which linkingly enters through at least one beam-penetrable (i.e. transparent) wall, or the said heating is diminished to such an extent, that disturbances of the function of interest within the microsystem are excluded.

Second, to be considered as a cooling adjunct, a heat conducting layer must be provided, by means of which layer an electrode surface is connected to a heat-sink, for instance, to the wall of the microsystem.

Third the cooling apparatus can be formed by an active component element (for instance, a Peltier-Element) which, advantageously, should be located proximal to the electrode in the microsystem.

The microsystem can be a fluidic or a liquid filled microsystem, in which the invented shielding of the electrode surfaces prevents the formation of electro-hydrodynamic flows. The microsystem can be designed for the manipulation of suspended particles or particles which tend to be adsorbed. In the case of the latter, the invented shielding prevents an undesired heating, for instance, of cells which are adsorbed onto electrodes.

The at least one reflector layer is formed by the electrode material itself, or by additional covering coatings and/or base layers in the electrodes, and/or masking lamination on the walls of the microsystem. The material of the reflector layer should be so selected, with consideration give to the wavelength range of interest, that the currently incident linking light is subjected to a higher index of refraction. The incoming beamed radiation, especially laser light, serves for the formation of at least one optical use (optical tweezer) in the microsystem or radiation for observation and/or measurement purposes.

In accord with advantageous embodiments of the invention, measures were taken on the electrodes, whereby a heating thereof, especially by exposure to light, is avoided. To these measures may be counted:

first, the at least partial formation of the electrodes from a material, which, for the specific incident light, is transparent, second the presence of heat conducting layers, by which the heat is transferred from the electrodes to the ambient environment, i.e., especially to the walls of the microsystem and/or to the liquid of the suspension.

Proximal to at least one electrode of the microsystem, a coaction zone is subjected to voltage, in which at least one particle can be treated with electrical and optical forces. Since even a focused laser beam has a finite beam cross-section, it can even happen that scatter radiation onto an electrode occurs, when the focus in the coaction zone is carried out at a distance from said electrode, especially from the end thereof. One object of the invention is providing the availability of specific forms of the electrodes, which, first, lessen the action of the scatter, and second assure a reliable activity of the electrical forces in the coaction zone.

A further object of the invention is the employment of materials which reflect in the infrared spectrum range, in particular, metals, semiconductors, or dielectrical compounds, suitable for at least a one-sided shielding of the electrodes in the micro system.

Another object of the invention is a microsystem constructed with at least one cooling arrangement, which microsystem is equipped with a light source for the incident linking of light for manipulation or measurement.

Another object of the invention is a procedure for the manipulation and/or analysis of samples with electrical forces in an invented fluidic microsystem.

An essential advantage of the invention exists in the increased functional security of the microsystem. Undesirable influences on the particles and/or the liquid medium of the suspension are avoided in the microsystem. In the microsystem, the previously mentioned gas bubble formation on the electrodes is excluded. The sensitivity of the microsystem in respect to faulty operations, such as the focusing of an optical tweezer onto an electrode is reduced.

BRIEF DESCRIPTION OF SEVERAL VIEWS OF THE DRAWINGS

Further advantages and details of the invention are evident from the following description with the aid of the attached drawings. There is shown in:

FIG. 1 a schematic perspective view of an invented microsystem,

FIG. 2 a schematic profile view of an invented microsystem for the illustration of various measures taken for the reduction of the heating of electrodes, FIGS. 3-5 schematic top views of electrode arrangements in an invented microsystem, and FIG. 6 a presentation of curves for the illustration of the transmission of ITO material.

DETAILED DESCRIPTION OF PREFERRED EMBODIMENTS OF THE INVENTION

Figure 3:
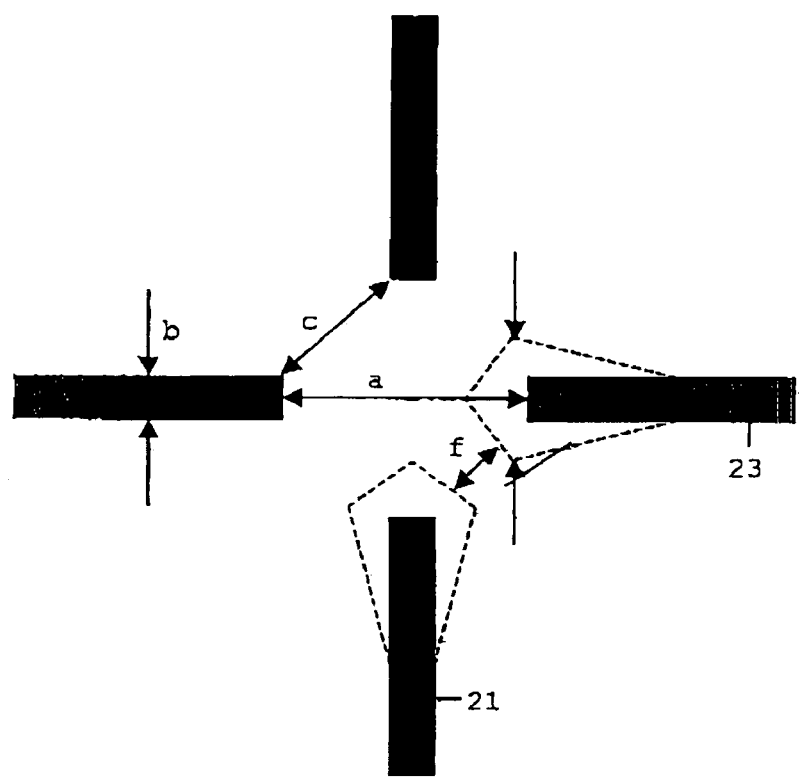

In the following, the invention will be described in reference to a fluidic, through-flow micro system. The invention is, however, not limited to this application, but can be put to use in other liquid filled microsystems having electrode arrays, for instance, including microsystems with Ion-Sensitive Field Effect Transistor methodology (ISFET) for analysis nerve cells or cancer cells (see above, P. Fromherz et al.) or in microsystems for the investigation of cell traces or cell adsorbents. The manufacture of microsystems is, per se, well known, and, on this account, need not be described here. The invented cooling apparatus on electrodes is advantageously effected by at least one shielding reflector layer. The reflector layer can be a continuous covering, or it may be interrupted by appropriate patterning.

FIG. 1 shows, in a schematic, perspective view, a compartment 10 of an invented microsystem 100. The compartment 10 is a portion of the provided channel and reservoir structure in the microsystem and, for instance, the said compartment is provided in a channel, which can have a through-flow in the direction of the arrow A of a liquid laden with suspended particles. On each side, the compartment 10 is bordered by wall structures, which here incorporate the cover 12, the bottom 13 and the sides 14. The electrode array 20 forms an octopole, which is designed for the establishment of a dielectric field cage. To this end, the electrodes 21 to 28 are electrically connected to supply lines (not shown) leading to a control device, which especially contains a high frequency generator for the buildup of a high frequency, electrical voltage between the electrodes.

By means of the electrode ends, which point to one another, in compartment 10 an coaction zone is created, in which, simultaneously with the electric field forces, also optical forces can be in action. In general, at this location, a partial area of the microsystem is designated as an coaction zone, in which particles are subjected to both electrical and well as optical forces. The partitioning against the surrounding space in the microsystem is constructed by the formation of the electrical fields (field barriers) between the electrodes and the optical cage, in accordance with the incident light entering.

In the case of the presented example, the top 12 of the compartment 10 is transparent, so that, corresponding to the incident direction B, a laser beam can be focused into the coaction zone 11. A particle 30 is captured in the focus 41.

The microsystem depicted in FIG. 1, possesses, for example, dimensions such as are described in the microsystem of G. Fuhr, et al., in *Applied Physics A* vol. 67, 1998, page 385. The width of the channel (i.e. width of the bottom and top sections) runs some 400 μm. The channel height, and thus the height of the side walls, is approximately 40 μm. The top and bottoms 12, 13 are comprised of glass and have thicknesses of respectively, 170 μm and 500 μm. The electrodes 21 to 28 are strip electrodes, applied photographically, which are disposed at approximately 90° from one another and placed on both the top 12 and the bottom 13. A laser ($\lambda$=700 . . . 1064) is beamed into the coaction zone 11. For this action, for example, a commercially available optical tweezer (for instance diode laser or Nd-YAG laser, as made by P.A.L.M., Bernried, Germany) is used, with a microscope Olympus IX 70. The microscope is equipped with an oil immersion objective (100-X enlargement, N.A.=1.3. The laser power runs, at the objective exit about 30 mW.

In the microsystem 100, on all electrodes 21 to 18 respectively, at least one reflector layer is provided. Each electrode is, at least on its end proximal to the coaction zone 11, shielded by the reflector layer against any incident laser beam B. Partial beams or parts of the beam field of the laser beam B, which are directed onto the electrodes, are reflected by the respective reflector layer. In accord with the invention, at least on the side of each electrode subject to the incoming beam, reflector layers are provided. For unusually shaped constructions, provision can be made, that on two sides, or even on all sides of the electrodes, reflector layers can be installed. This is necessary, for example, if the microsystem is designed for optional beam radiation through the top or bottoms 12, 13 of the compartment 10. Such complete installation of reflective layer is also necessary to exclude the action of back reflections within the microsystem, for example from the upper side of lower electrodes 21-24 onto the underside of the upper electrodes 25-28.

In the case of the embodiment shown in FIG. 1, the electrodes 21-28, themselves, consist of material which reflects in the infrared spectrum, such as gold, copper or aluminum. The electrode strips, with a thickness of about 1000 nm to 1 μm are applied directly on the glass top and bottom .

A test of the microsystem 100 is done with latex beads (effective diameter 1 μm, made by Polyscience) serving as flow markers and also done with yeast cells (diameter about 5 μm, fixated with glutar-aldehyde) serving as capture objects. Distilled water is used as the suspension liquid. By the control of the electrodes 21-28 for the establishment of the dielectric field cage in the rotational mode, with microscopic observation it is shown, that the compartment 10 has an undisturbed throughput of the latex beads (no turbulence) while the yeast cells could be securely restrained in the dielectric field cage and manipulated in the focus of the optical tweezer. In this action, even in the case of direct beam radiation of the electrodes, no formation of bubbles was detected.

Further embodiments of the invented cooling apparatus are illustrated in the schematic, profile view of a microsystem 100 in FIG. 2. The different variants can be provided all at the same time and place, or individually.

In this side view, looking in the direction of the length of the channel, i.e., the y-axis, principally the top and bottoms 12, 13 of the compartment 10 are shown. The layer shaped appearance of the electrodes 21, 22 and 25, 26 is schematically depicted. In the case of presented in FIG. 2, the linkage of the laser beam B through the bottom 13 is provided. The reference number 40 designates the objective of the microscope for the entry of the laser beam.

The electrodes shown in FIG. 2 possess a multi-layer construction. In the way of example, the electrode 21 consists of the electrode layer 21a and a base layer 21b (so-called "plating base"). The thicknesses of the electrode and the base layer 21a, 21b run, respectively, 130 nm and 20 nm. In accord with one embodiment of the invention, the base layer 21b is designed as the reflector layer. Materials employed for the base layer would be, for example, gold, aluminum or a dielectric compound with a fitting index of refraction.

In the case of the electrode 26, an additional variant of a reflective layer is demonstrated. The electrode layer 26a carries, on the side proximal to the compartment a cover layer 26b, which advantageously, is applied in the same manner as the above mentioned base layer 21b. With the presence of the reflecting top and/or bottom base layers, the electrode layers can be constructed from a non-reflecting material. This is in relation to the use of possibly expensive materials, or materials which are difficult to work, since the top and bottom electrode layers can be made thinner than the electrode layers.

The invented reflector layer can also be made as a mask, independent of the electrodes. This is illustrated in the case of the electrodes 22 and 25. An external layer 22b or an internal layer 25b can provided as masking, which is to be found on the side, from which beams can be expected directed to the coaction zone 11. The masked internal or external on the top or bottoms 12, 13 possess in the incident beam direction B, advantageously a larger surface than the respective shielded electrodes. The masking can also be made as a continuous layer, which principally leaves open an entry window 42 to accommodate the entry of the laser beam. The inner and the out layers have a thickness with a range, for instance, of 50 to 10 nm and are composed of a material with a high coefficient of reflection.

In FIG. 2, electrode 22 illustrates a further measure, in accord with the invention, for the reduction of the heat application of electrodes. A heat conducting layer 50 is provided as a cooling means, which is in good thermal contact with the electrode layer 22a. The connection is made by the side edges of the electrode layers and the heat conduction layers, namely 22a and 50. The connection can also be made by an intermediate layer 51, which is made of the same material as heat conducting layer 50 (for instance, gold). The heat conducting layer 50 and, possibly, the intermediate layer 51 are electrically insulated from the electrode layer 22a by dielectric layers (not shown).

For precision centered applications, or in the case of angular incident beams, (arrow C) it can be necessary, that on the electrodes, side reflector shielding layers be installed. This is illustrated in the case of electrode 26 with the side layer 26c, which is essentially designed the same as the top and base layers, 21b, 26b.

Where electrode 21 is concerned, there is provided a cooling apparatus as a further embodiment of the invention, wherein, in the bottom, an installed cooling element 21c is shown. The cooling element 21c stands in thermal contact with the electrode 21 and is located under this electrode or is offset to one side. The cooling element is, for instance, a Peltier-Element. Alternative to its integration in the bottom 13, the cooling element 21c can also be installed from the outside, (as a kind of cooling finger) on the wall of the compartment.

Deviating from the embodiments illustrated in FIGS. 1 and 2, in a microsystem, in accord with the invention, the electrode arrangement can be principally positioned on one side of a wall of the compartment 10, while non-metallized, thin glass would be on the opposite wall side.

For the reduction of the heat to which the electrodes are subjected, in keeping with the invention, an optimizing of the geometrical characteristics of the electrode array can be provided. This is particularly of interest where quadripole and octopole electrode arrangements are concerned. The smaller the electrodes are, and the larger their distance from the coaction zone 11 is, (that is, their mutual separation), just so much less is the scatter beaming on the electrode ends or the corresponding reflector layers. In any case, the separating distance must not be all too great, if the electrical field force in the coacting zone 11 is going to be effectively used. Greater separating distances of the electrodes can only be compensated for by greater voltage within certain limits. The inventors have determined, that for typical applications in the dielectrical manipulation of biological particles with the simultaneous usage of optical tweezers, under the above named conditions, the geometrical parameters (size, shape) of the electrodes can be optimized. This is illustrated in the FIGS. 3 and 4.

In FIG. 3, the strip form of a quadripole or the electrode plane of an octopole is presented. Optimal electrode parameters for a width b lie within an range of 20 to 25 µm, and the separating distance a from the opposite electrodes runs about 35 to 45 µm, preferably, 40 µm, and the separating distance from the adjacent electrode is about 20 to 25 µm. Under these geometric conditions, a secure dielectric retention of particles in the dielectric field cage, with the least light-induced flow, is possible.

If the electrodes do not possess the rectangular strip, but rather have the outline indicated by the dotted lines shown in electrodes 21 and 23, thus with broadened electrode ends, then the following parameter ranges are optimal:

Width of the electrode ends d: 30-35 µm, separating distance f to neighboring electrodes, 15-20 µm, separating distance to oppositely placed electrodes, corresponding to a, 35-45 µm, preferably 40 µm.

With these dimensions, the function of the dielectric field cage, as compared to the strip form electrodes is essentially improved.

Figure 4:
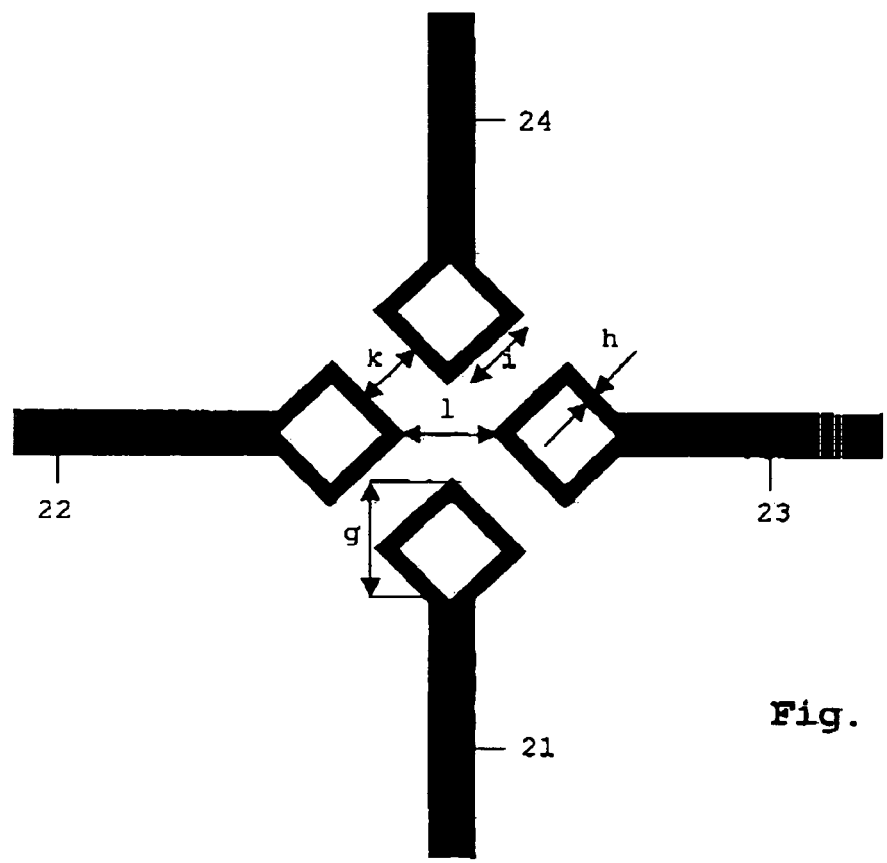

An optimized electrode shape is illustrated in FIG. 4. The end surfaces of the electrodes 21-24, which face the coaction zone 11, are cut out to form frames of electrode strips, so that the stressed electrode surfaces, as seen in projection from the direction of the incident radiation, are reduced. The following dimensional parameters proven themselves as optimal for achieving an effective dielectric manipulation of particles in a field cage:

length g of the end surfaces, ca. 20 µm.

width h of the electrode strips, ca. 5-10 µm, side length i of the electrode strips, ca. 20 µm, perpendicular separating distance k of the frames, ca. 15 µm, and separating distance l of the opposite frames, ca 40 µm, The design of the electrodes as cutout frames, has the advantage, that in the case of an uniformly maintained electrical field activity, the effective absorbent electrode surface is diminished. Instead of the illustrated frame shape, the electrode ends can also be in the form of arrow heads.

Figure 5:
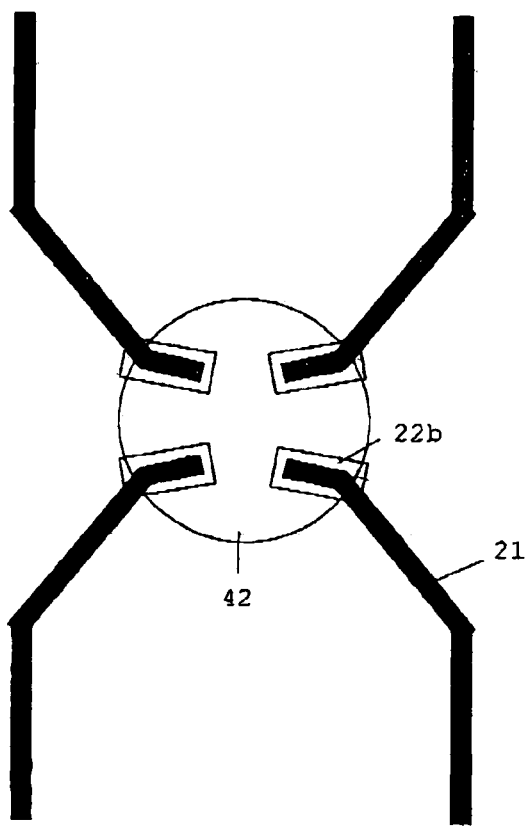

FIG. 5 illustrates the arrangement of masked external layers 22b (also see FIG. 2) in a schematic top view. The outside layers 22b, are on the side proximal to the objective, that is to say, they are placed on the bottom of the compartment. It is not a necessity, that the external layers 22b cover all the surface of an electrode (for instance 21).

Much more, it is sufficient, if a shielding in the coaction zone is provided, which zone is, in FIG. 5, outlined as a circle 42 and in which the electric field of the electrodes and the operational area of the optical tweezers are effectively active.

Figure 6:
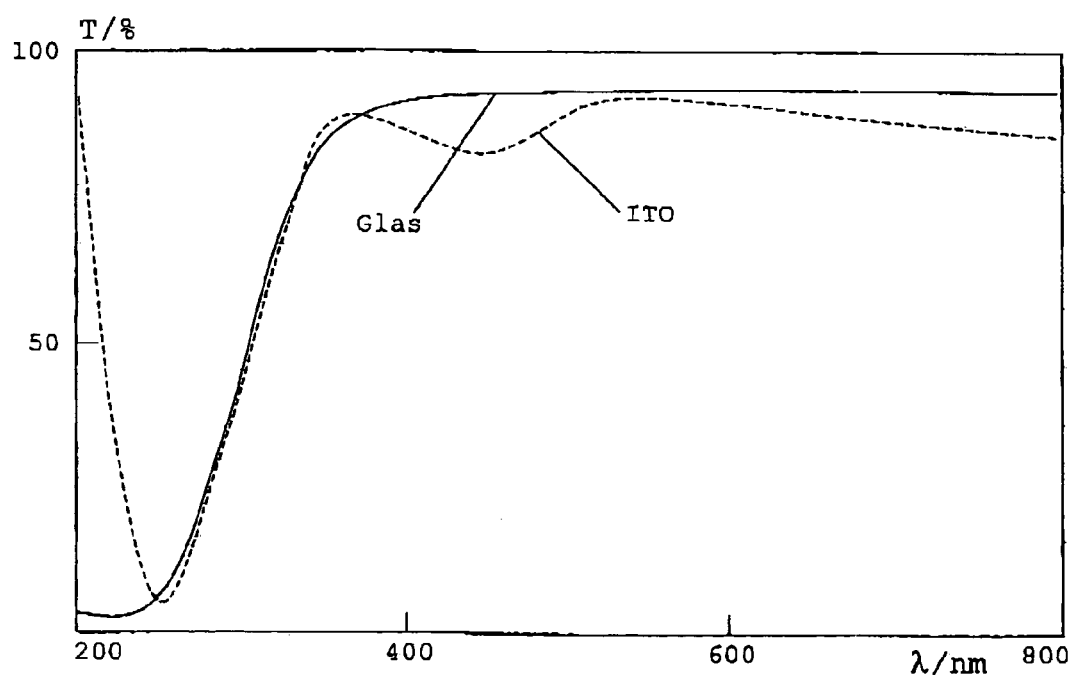

In accord with an advantageous embodiment of the invention the electrodes themselves are made from a material which transmits the currently employed spectral range. By a combination of dielectrical field forces and optical tweezers, it is advantageous to use indium-tin-oxide (ITO), which has a high degree of transmission for wave lengths above 400 nm and is especially transparent in regard to the infrared spectrum. This infrared transparency approaches that of glass. This is illustrated in the presentation of the curves in FIG. 6.

The disclosed features in the foregoing description, in the drawings, and the claims can be of meaning both individually as well as in optional combination for the realization of the invention it its various formulations.

The invention claimed is:

1. A fluidic microsystem comprising:
    at least one compartment for receiving and/or passing through of a liquid, wherein the compartment includes at least one wall through which electromagnetic radiation can be linked into a coaction zone corresponding to a predetermined incident direction of a beam of the electromagnetic radiation;
    an electrode arrangement including at least one electrode, wherein the electrode arrangement defines the coaction zone; and
    a cooling apparatus provided on the at least one electrode, wherein the cooling apparatus comprises at least one member selected from the group consisting of:
    at least one reflector layer adapted to at least partially shield the at least one electrode from the beam;
    at least one heat conducting layer through which the at least one electrode stands in thermal communication with a wall of the compartment; and
    an active cooling element in direct contact with the at least one electrode.

2. The microsystem of claim 1, wherein the reflector layer comprises the at least one electrode, and at least one of the following: (a) at least one covering layer on a side of the at least one electrode proximal to the compartment; (b) at least one base layer on a side of the at least one electrode proximal to a wall of the compartment; (c) at least one interior layer on a wall of the compartment; and (d) an external layer.

3. The microsystem of claim 2, wherein the at least one covering layer or the at least one base layer has the same shape as the at least one electrode in a projection direction parallel to the incident direction of the beam.

4. The microsystem of claim 2, wherein the at least one interior layer or the external layer forms a mask, which is at least as large as the at least one electrode in a projection direction parallel to the incident radiation direction of the beam.

5. The microsystem of claim 1, wherein the at least one reflector layer comprises a metal or a metal alloy with a reflection coefficient in an infrared spectral range, the reflection coefficient being at least as large as an infrared reflection coefficient of copper, aluminum or gold.

6. The microsystem of claim 5, wherein the at least one electrode comprises indium-tin-oxide (ITO).

7. The microsystem of claim 1, wherein the at least one reflector layer comprises at least one dielectric layer or gradient layer with a reflection coefficient in an infrared spectral range, the reflection coefficient being at least as large as an infrared reflection coefficient of copper, aluminum or gold.

8. The microsystem of claim 1, wherein the at least one electrode comprises a material transparent in an infrared spectral range.

9. The microsystem of claim 1, wherein a light source having a fixed beam direction adjustable relative to the coaction zone is placed outside of the compartment.

10. The microsystem of claim 9, wherein the light source is an infrared laser.

11. A process for manipulating and/or analyzing a sample with electrical forces in a fluidic microsystem, said process comprising:

providing a microsystem of claim 1;

providing the sample in the at least one compartment of the microsystem; and applying the electrical forces to the sample to manipulate and/or analyze the sample.

12. The process of claim 11, wherein the sample comprises DNA or protein.

13. The process of claim 11, wherein the sample comprises a biological cell.

14. The process of claim 11, wherein the sample is analyzed as a step in a materials research study or a combinatorial chemistry study.

* * * * *